April 13, 1971 F. R. WELLS Plant Pat. 3,046
ALMOND TREE
Filed July 22, 1969
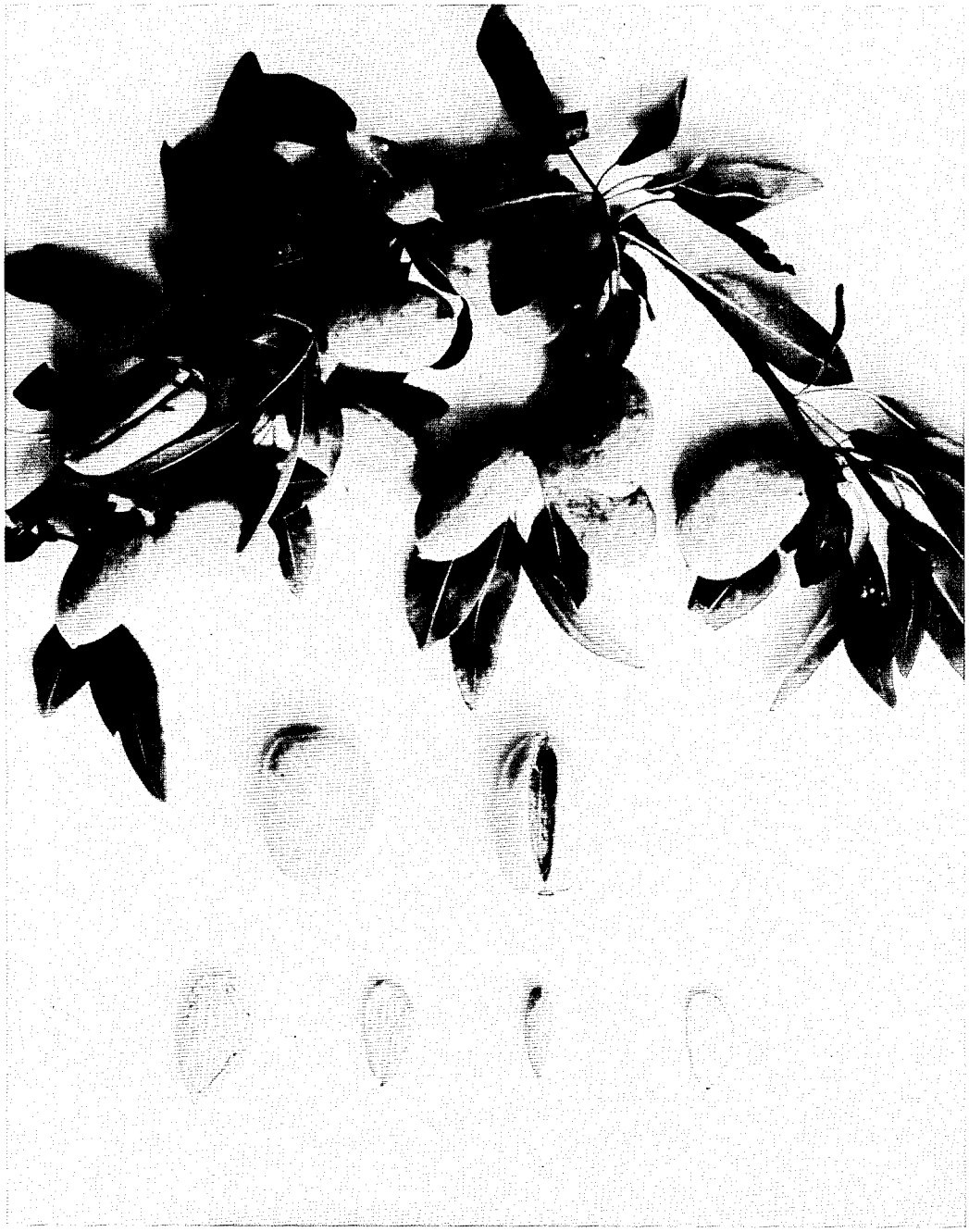
INVENTOR
Frederick R. Wells
BY
Webster & Webster
ATTORNEYS

United States Patent Office

Plant Pat. 3,046
Patented Apr. 13, 1971

3,046
ALMOND TREE

Frederick R. Wells, Rte. 3, Box 80-A,
Chico, Calif. 95926

Filed July 22, 1969, Ser. No. 844,675
Int. Cl. A01h *5/03*
U.S. Cl. Plt.—30 1 Claim

ABSTRACT OF THE DISCLOSURE

A variety of almond tree which is of medium size, vigorous and dense in growth with abundant foliage, blooms heavily, and is a regular and very heavy producer of nuts well distributed on the tree; the nuts being large, having a high percentage of kernel to shell, and of a form more elongated than the nuts of the Nonpareil and which the present variety most nearly resembles.

ORIGIN OF THE VARIETY

The present variety of almond tree was discovered by me, growing as a chance seedling in a fence row, on my ranch located near Chico, in the County of Butte, State of California. Such chance seedling was, upon its discovery, subsequently observed quite carefully and I recognized that it was quite distinct from other varieties of almonds.

ASEXUAL REPRODUCTION OF THE VARIETY

Subsequent to its discovery and recognition of its novel and distinctive characteristics, I asexually reproduced the present variety of almond tree by grafting, on Lovell (unpatented) peach rootstock, on my ranch located as aforesaid; such reproductions having run true to the original tree in all respects.

SUMMARY OF THE VARIETY

The herein claimed variety of almond tree, in comparison to the Nonpareil (unpatented) and which is the previously known variety which resembles it most closely in general respects, is characterized, as to novelty, by:

A tree which is of medium size, vigorous and dense in growth, with abundant foliage; the leaves being slightly more glossy and larger than those of the Nonpareil.

A tree which blooms heavily about with the Nonpareil, and is a regular and very heavy producer of large nuts having a high percentage of kernel to shell and of a form more elongated than the nuts of the Nonpareil; the kernels being of good quality and having much the same flavor as said Nonpareil.

The instant variety is further characterized by apparently being self-pollinating, and having substantial resistance to disease; these factors being evidenced, respectively, by the heavy bearing (with few bud-drops) of the original tree although a substantial distance from any potential pollinizer tree, and by the absence of any dead or diseased wood in the original tree even though it has never been sprayed or pruned.

BRIEF DESCRIPTION OF THE DRAWING

The drawing is a photographic reproduction in color illustrating twigs with attached nuts, detached nuts both in and out of hull, and kernals out of shell; one kernel being cut to expose the meat.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Medium.
- *Vigor.*—Vigorous.

Trunk:
- *Form.*—Stocky.
- *Texture.*—Shaggy.

Branches:
- *Form.*—Medium.
- *Texture.*—Smooth.
- *Branching habit.*—Upright.
- *Color.*—New wood—Green.

Foliage:
- *Quantity.*—Abundant.

Leaves:
- *Size.*—Large; average length—3"; average width—1".
- *Form.*—Lanceolate; acutely pointed.
- *Thickness.*—Medium.
- *Texture.*—Smooth.
- *Margin.*—Finely serrate.
- *Petiole.*—Medium length; medium thickness.
- *Glands.*—Average number—2; opposite; small; globose; green; positioned at junction of leaf and petiole.
- *Stipules.*—None.
- *Color.*—Top Side—glossy medium green (22-L-8); under side—lighter green (22-L-6).

Bloom:
- *Amount of bloom.*—Very heavy.
- *Color.*—White.
- *Blooming period.*—March 2, 1969–March 24, 1969; approximately (2 days earlier) with Nonpareil.

Crop:
- *Bearing.*—Regular bearer.
- *Productivity.*—Very heavy.
- *Distribution of nuts on tree.*—Well distributed .
- *Harvest period.*—Medium, as compared to Nonpareil.
- *Tenacity.*—Hangs well on tree, easy to harvest, easy to hull.

Hull:
- *Outer surface.*—Smooth.
- *Form.*—Irregular.
- *Thickness.*—Thick.
- *Flesh.*—Fleshy.
- *Suture.*—Flat depressed.
- *Color.*—Light yellow green (21-K-4), with short silvery pubescence.
- *Dehiscence.*—Opens freely.
- *Splitting.*—Along suture.

Nut:
- *Size.* — Large. Average length — 1½"; average width—⅝"; average thickness—½".
- *Form.*—Length/width — elongated; width/thickness—plump.
- *Shell.*—Paper. Outer shell—crumbling; largely missing. Inner shell—Soft; poorly sealed.
- *Color.*—Macaroon (12-H-7).
- *Pits.*—Small; numerous; shallow.
- *Base.*—Ventrally oblique; dorsally oblique.
- *Stem scar.*—Small; acute.
- *Apex.*—Acute; sharp; prolonged at tip.
- *Wing.*—Narrow; thin; tapered toward apex.
- *Inner surface.*—Light colored.
- *Percentage of kernel to nut.*—72.21%.

Kernel:
- *Size.*—Large; average length—1¼"; average width—9/16"; average thickness—5/16".
- *Form.* — Length/width — elongated; width/thickness—medium.

*Base.*—Ventrally oblique.
*Stem scar.*—Small; obtuse.
*Apex.*—Accuminate; sharp.
*Plumpness.*—Smooth.
*Pellicle.*—Thin.
*Pubescence.*—Smooth.
*Color.*—Light tan (13–L–8).
*Number of doubles.*—None.
*Flavor.*—Dry; sweet.
*Quality.*—Good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is of medium size, vigorous and dense in growth with abundant foliage, and the leaves being slightly more glossy and larger than those of the Nonpareil; the tree—which blooms heavily about with the Nonpareil—being a regular and very heavy producer of large nuts having a high percentage of kernel to shell, and the nuts being more elongated than those of said Nonpareil.

No references cited.

ROBERT E. BAGWILL, Primary Examiner